(12) United States Patent
Soucaille et al.

(10) Patent No.: US 8,298,807 B2
(45) Date of Patent: Oct. 30, 2012

(54) MICRO-ORGANISMS FOR THE PRODUCTION OF 1,2-PROPANEDIOL OBTAINED BY A COMBINATION OF EVOLUTION AND RATIONAL DESIGN

(75) Inventors: Philippe Soucaille, Deyme (FR); Francois Voelker, Montrond les Bains (FR); Rainer Figge, Riom (FR)

(73) Assignee: Metabolic Explorer, Saint Beauzire (FR)

( * ) Notice: Subject to any disclaimer, the term of this patent is extended or adjusted under 35 U.S.C. 154(b) by 308 days.

(21) Appl. No.: 12/532,405

(22) PCT Filed: Mar. 21, 2008

(86) PCT No.: PCT/EP2008/053445
§ 371 (c)(1),
(2), (4) Date: Sep. 21, 2009

(87) PCT Pub. No.: WO2008/116852
PCT Pub. Date: Oct. 2, 2008

(65) Prior Publication Data
US 2010/0285547 A1  Nov. 11, 2010

(30) Foreign Application Priority Data
Mar. 23, 2007 (WO) ............... PCT/IB2007/001680

(51) Int. Cl.
*C12N 1/20* (2006.01)
*C12Q 1/68* (2006.01)
*C07H 21/04* (2006.01)

(52) U.S. Cl. .............. 435/252.33; 435/6.1; 536/23.2

(58) Field of Classification Search .................. None
See application file for complete search history.

(56) References Cited

U.S. PATENT DOCUMENTS

| | | | |
|---|---|---|---|
| 6,087,140 | A | 7/2000 | Cameron et al. |
| 6,303,352 | B1 | 10/2001 | Cameron et al. |
| 2005/0054060 | A1 | 3/2005 | Chateau et al. |
| 2007/0072279 | A1 | 3/2007 | Meynial-Salles et al. |

FOREIGN PATENT DOCUMENTS

WO  2004033646  4/2004

OTHER PUBLICATIONS

International Search Report for PCT/EP2008/053445, dated Jul. 7, 2008 (2 pages).
Badia et al., "Fermentation Mechanism of Fucose and Rhamnose in *Salmonella typhimurium* and *Klebsiella pneumoniae*," Journal of Bacteriology, Jan. 1985, pp. 435-437.
Tran-Din et al., "Formation of D(−)-1,2-propanediol and D9-)-lactate from glucose by *Clostridium sphenoides* under phosphate limitation," Arch Microbiol (1985), 142:87-92.
Cameron et al., "A Novel Fermentation: the Production of R(−)-1,2-Propanediol and Acetol by *Clostridium thermosaccharolyticum*," Bio/Technology, Jul. 1986, vol. 4, pp. 651-654.
Sanchez-Riera et al., "Influence of Environmental Factors in the Production of R(−)-1,2-Propanediol by *Clostridium thermosaccharolyticum*," Biotechnology Letters (1987), vol. 9, No. 7, pp. 449-454.
Altaras et al., "Metabolic Engineering of a 1,2-Propanediol Pathway in *Escherichia coli*," Applied and Environmental Microbiology, Mar. 1999, pp. 1180-1185.
Cameron et al., "Metabolic Engineering of Propanediol Pathways," Biotechnol. Prog. 1998, 14, pp. 116-125.
Altaras et al., "Enhanced Production of (R)-1,2-Propanediol by Metabolically Engineered *Escherichia coli*," Biotechnol. Prog. 2000, 16, pp. 940-946.
Huang et al., "Characterization of Methylglyoxal Synthase from *Clostridium acetobutylicum* ATCC 824 and Its Use in the Formationof 1,2-Propanediol," Applied and Environmental Microbiology, Jul. 1999, pp. 3244-3247.
Berrios-Rivera et al., "The effect of carbon sources and lactate dehydrogenase deletion on 1,2-propanediol production in *Escherichia coli*," J. Ind. Microbiol. Biotechnol. 2003, 30:34-40.
Datsenko et al., "One-step inactivation of chromosomal genes in *Escherichia coli* K-12 using PCR products," PNAS, Jun. 6, 2000, vol. 97, No. 12, pp. 6640-6645.
Anderson, "Growth Requirements of Virus-Resistant Mutants of *Escherichia coli* Strain "B"," Proc. N.A.S., Mar. 21, 1946, pp. 120-128.
Schaefer et al., "Automated Sampling Device for Monitoring Intracellular Metabolite Dynamics," Analytical Biochemistry (1999), 270, pp. 88-96.
Wiesenborn et al., "Thiolase from *Clostridium acetobutylicum* ATCC 824 and Its Role in the Synthesis of Acids and Solvents," Applied and Environmental Microbiology, Nov. 1988, pp. 2717-2722. Monot et al., "Acetone and Butanol Production by *Clostridium acetobutylicum* in a Synthetic Medium," Applied and Environmental Microbiology, Dec. 1982, pp. 1318-1324.
Vasconcelos et al., "Regulation of Carbon and Electron Flow in *Clostridium acetobutylicum* Grown in Chemostat Culture at Neutral pH on Mixtures of Glucose and Glycerol," Journal of Bacteriology, Mar. 1994, pp. 1443-1450.

*Primary Examiner* — Anand Desai
(74) *Attorney, Agent, or Firm* — Baker Donelson Bearman, Caldwell & Berkowitz, PC

(57) ABSTRACT

The present invention concerns a new method combining evolution and rational design for the preparation of a strain of micro-organism for the production of 1,2-propanediol from a carbon source. The said method comprises growing an initial strain under selection pressure in an appropriate growth medium, said initial bacterial strain comprising an attenuation of the expression of the tpiA gene and an attenuation the expression of at least one gene involved in the conversion of methylglyoxal to lactate, in order to promote evolution in said initial strain; then selecting and isolating the evolved strain having an increased 1,2 propanediol production rate; then reconstructing a functional tpiA gene in the evolved strain. The present invention also concerns the evolved strain such as obtained, that may be furthermore genetically modified in order to optimize the conversion of a carbon source into 1,2-propanediol without bv-products and with the best possible yield.

9 Claims, 1 Drawing Sheet

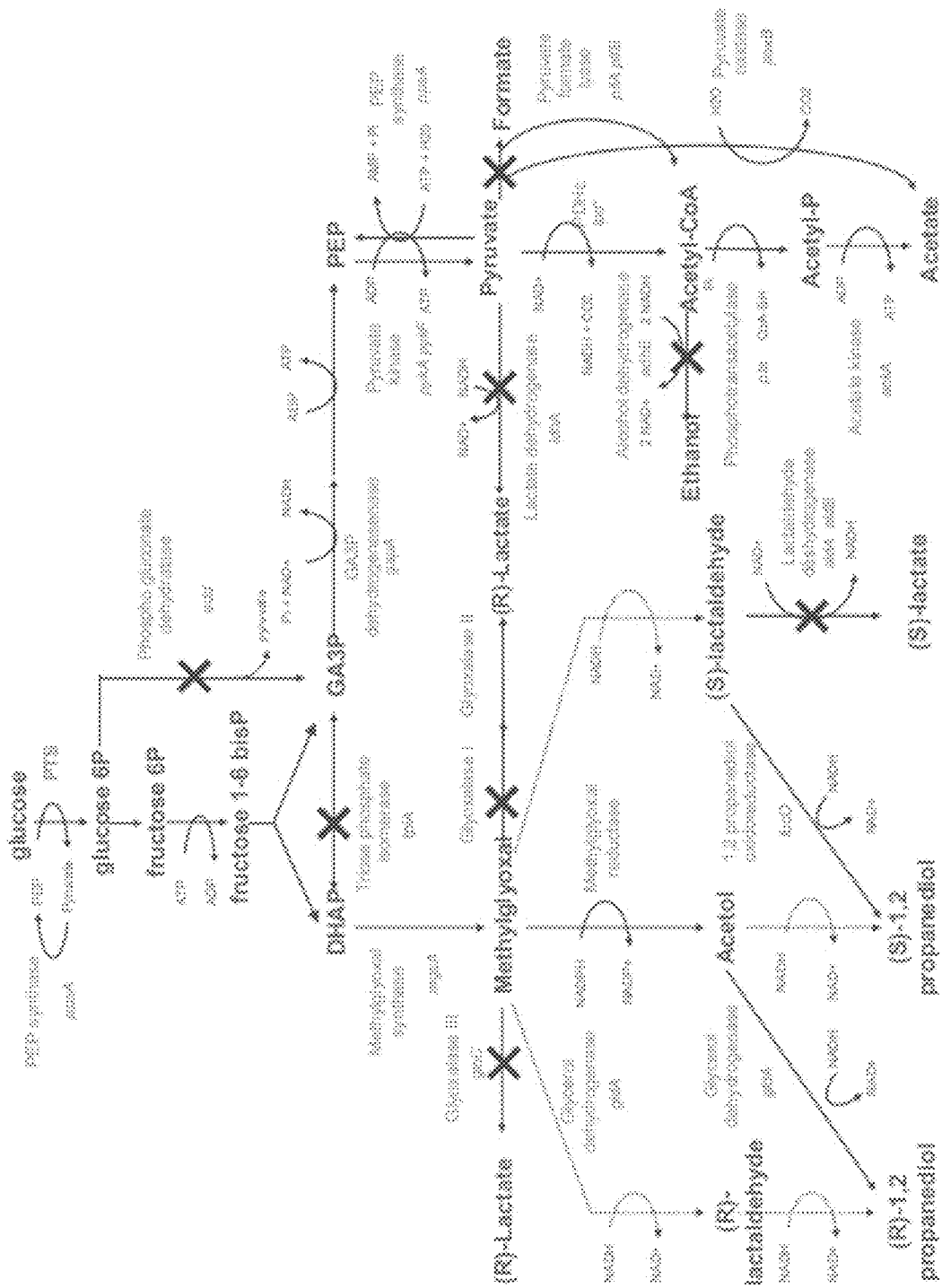

US 8,298,807 B2

MICRO-ORGANISMS FOR THE PRODUCTION OF 1,2-PROPANEDIOL OBTAINED BY A COMBINATION OF EVOLUTION AND RATIONAL DESIGN

CROSS REFERENCE TO RELATED APPLICATIONS

This application is a §371 National Stage Application of PCT/EP2008/053445 filed Mar. 21, 2008, which claims priority to PCT/IB2007/001680 filed Mar. 23, 2007.

BACKGROUND OF THE INVENTION

1. Field of the Invention

The present invention concerns a new method combining evolution and rational design for the preparation of a micro-organism to produce 1,2-propanediol, the micro-organism thereby obtained and its use for the preparation of 1,2-propanediol.

2. Description of Related Art 1,2-propanediol or propylene glycol, a C3 dialcohol, is a widely-used chemical. It is a component of unsaturated polyester resins, liquid detergents, coolants, anti-freeze and de-icing fluids for aircraft. Propylene glycol has been increasingly used since 1993-1994 as a replacement for ethylene derivatives, which are recognised as being more toxic than propylene derivatives.

1,2-propanediol is currently produced by chemical means using a propylene oxide hydration process that consumes large amounts of water. Propylene oxide can be produced by either of two processes, one using epichlorhydrin, and the other hydroperoxide. Both routes use highly toxic substances. In addition, the hydroperoxide route generates by-products such as tert-butanol and 1-phenyl ethanol. For the production of propylene to be profitable, a use must be found for these by-products. The chemical route generally produces racemic 1,2-propanediol, whereas each of the two stereoisomers (R)1,2-propanediol and (S)1,2-propanediol are of interest for certain applications (e.g. chiral starting materials for specialty chemicals and pharmaceutical products).

The disadvantages of the chemical processes for the production of 1,2-propanediol make biological synthesis an attractive alternative. Two routes have been characterized for the natural production of 1,2-propanediol from sugars by microorganisms.

In the first route 6-deoxy sugars (e.g. L-rhamnose or L-fucose) are cleaved into dihydroxyacetone phosphate and (S)-lactaldehyde, which can be further reduced to (S)-1,2-propanediol (Badia et al, 1985). This route is functional in *E. coli*, but can not yield an economically feasible process due to the elevated cost of the deoxyhexoses.

The second route is the metabolism of common sugars (e.g. glucose or xylose) through the glycolysis pathway followed by the methylglyoxal pathway. Dihydroxyacetone phosphate is converted to methylglyoxal that can be reduced either to lactaldehyde or to acetol. These two compounds can then undergo a second reduction reaction yielding 1,2-propanediol. This route is used by natural producers of (R)-1,2-propanediol, such as *Clostridium sphenoides* and *Thermoanaerobacter thermosaccharolyticum*.

*Clostridium sphenoides* has been used to produce 1,2-propanediol at a titer of 1.58 g/l under phosphate limited conditions (Tran Din and Gottschalk, 1985). *Thermoanaerobacter thermosaccharolyticum* has also been investigated for the production of 1,2-propanediol (Cameron and Cooney, 1986, Sanchez-Rivera et al, 1987). The best performances obtained were a titer of 9 g/l and a yield from glucose of 0.2 g/g. However, the improvement of the performances obtained with these organisms is likely to be limited due to the shortage of available genetic tools.

Cameron et al (1998) have investigated the use of *E. coli* as a platform for metabolic engineering for the conversion of sugars to 1,2-propanediol. Their theoretical analysis showed that the upper limit of the realistic product yield (considering mass balances and production of energy for growth) is significantly different depending on the culture conditions. Under anaerobic conditions, acetate will be produced as a by-product in order to recycle the reduced co-factors and the best yield shall be limited to 1 mole of 1,2-propanediol per mole of glucose (0.42 g/g). Under aerobic conditions, recycling of co-factors shall be ensured by the respiratory chain using oxygen as terminal electron acceptor and it could become possible to produce 1,2-propanediol without the production of by-products. Under these conditions, yield could reach at best 1.42 mol/mol (0.6 g/g). Considering the maximum titer of 1,2-propanediol, Cameron et al discussed its dependence on product and by-product toxicity. 1,2-propanediol is significantly less toxic than 1,3-propanediol and *E. coli* exhibits a residual growth rate of 0.5 $h^{-1}$ with 100 g/l 1,2-propanediol. The inhibition of growth is more likely to be due to the by-product acetate that is known to be highly growth inhibiting. Development of an anaerobic process for the production of 1,2-propanediol with high titers and yields will have to address the acetate issue. Conversion of acetate into acetone, which is less inhibitory and easily removed in situ has been proposed (WO 2005/073364).

Several investigations for genetic modifications of *E. coli* in order to obtain a 1,2-propanediol producer using simple carbon sources have been done by the group of Cameron (Cameron et al, 1998, Altaras and Cameron, 1999, Altaras and Cameron, 2000) and the group of Bennett (Huang et al, 1999, Berrios-Rivera et al, 2003). These studies rely on the one hand on the expression of one or several enzymatic activities in the pathway from dihydroxyacetone phosphate to 1,2-propanediol and on the other hand on the removal of NADH and carbon consuming pathways in the host strain. The best results obtained by the group of Cameron are production of 1.4 g/l 1,2-propanediol in anaerobic flask culture with a yield of 0.2 g/g of glucose consumed. When extrapolated to an anaerobic fed-batch fermenter, the production was 4.5 g/l 1,2-propanediol with a yield of 0.19 g/g from glucose, far from the theoretical evaluation of Cameron et al. These performances have been obtained with the overexpression of the methylglyoxal synthase gene of *E. coli* (mgs), the glycerol dehydrogenase gene of *E. coli* (gldA) and the 1,2-propanediol oxidoreductase gene of *E. coli* (fucO) in a strain lacking the gene coding for lactate dehydrogenase (ldhA). Results obtained with the same approach but with lower titers and yields are also described in the patents U.S. Pat. No. 6,087,140, U.S. Pat. No. 6,303,352 and WO 98/37204.

The group of Bennett also used an *E. coli* host strain lacking ldhA for the overexpression of the mgs gene from *Clostridium acetobutylicum* and the gldA gene from *E. coli*. Flask cultures under anaerobic conditions gave a titer of 1.3 g/l and a yield of 0.12 g/g whereas microaerobic cultures gave a titer of 1.4 g/l with a yield of 0.13 g/g.

An alternative method to obtain a strain producing 1,2-propanediol is to direct the evolution of an "initial strain" towards a state where the "evolved strain" produces the desired compound with better characteristics. This method is based on the natural evolution of a microorganism which is first modified by attenuation of two genes, tpiA and one gene involved in the conversion of methylglyoxal into lactate. The purpose for attenuating the tpiA gene coding for triose phosphate isomerase is to separate the two metabolic branches starting at glyceraldehyde-3-phosphate (GA3P) and dihydroxyacetone phosphate (DHAP) that are normally interconverted by this enzyme. The pathway from DHPA to 1,2-propanediol will be the "reducing branch" consuming reduced co-factors (NADH), whereas the metabolism from GA3P to acetate will be the "oxidative branch" producing NADH and energy for the growth of the cell. Without a functional tpiA gene, the metabolism of the cell is "locked" and the growth of the strain, the production of 1,2-propanediol and the production of acetate are tightly coupled. Under selection pressure in an appropriate growth medium, this initial strain will evolve to a state where the production of 1,2-propanediol by said strain is improved. This procedure to obtain an "evolved strain" of micro-organism for the production of 1,2-propanediol is described in the patent application WO 2005/073364. This evolution process and the following step of fermentation are preferentially performed under anaerobic conditions. This technology is a clear improvement over the prior art. A 1,2-propanediol titer of 1.8 g/l was obtained, with a yield of 0.35 gram per gram of glucose consumed, close to the theoretical result of Cameron et al.

The object of the present invention is the improvement of an 1,2-propanediol producer strain by evolution and subsequent rational genetic engineering of the evolved strain. A special feature is the reconstruction of a functional tpiA gene in the evolved tpiA minus strain. These modifications lead to an improved production of 1,2-propanediol.

DESCRIPTION OF THE INVENTION

The present invention concerns a new method combining evolution and rational design for the preparation of a strain of micro-organism for the production of 1,2-propanediol from a carbon source. The said method comprises:
  growing an initial strain under selection pressure in an appropriate growth medium, said initial bacterial strain comprising an attenuation of the expression of the tpiA gene and an attenuation the expression of at least one gene involved in the conversion of methylglyoxal to lactate (such as gloA, aldA, aldB), in order to promote evolution in said initial strain,
  then selecting and isolating the evolved strain having an increased 1,2 propanediol production rate (increased by at least 20%),
  then reconstructing a functional tpiA gene in the evolved strain;

In one aspect of the invention, the synthesis of unwanted by-products is attenuated by deleting the genes coding for enzymes involved in synthesis of lactate from pyruvate (ldhA), formate (pflA, pflB), ethanol (adhE). In another aspect of the invention, the Entner-Doudoroff pathway is eliminated by deleting either the edd or eda gene or both. Advantageously, in order to make more NADH available for the reduction steps in the biosynthesis pathway of 1,2-propanediol, at least one gene selected among arcA and ndh is attenuated.

The microorganism used for the preparation of 1,2-propanediol is selected among bacteria, yeasts and fungi, but is preferentially from the species *Escherichia coli* or *Clostridium acetobutylicum*.

The present invention also concerns the evolved strain such as obtained, that may be furthermore genetically modified in order to optimize the conversion of a carbon source into 1,2-propanediol without by-products and with the best possible yield. In one aspect of the invention, the glyceraldehyde 3 phosphate dehydrogenase activity is reduced in order to redirect a part of the available glyceraldehyde 3 phosphate toward the synthesis of 1,2-propanediol. In another aspect of the invention, the efficiency of the sugar import is increased, either by using a sugar import independent of phosphoenolpyruvate (PEP) like the one encoded by galP, or by providing more PEP to the sugar-phosphotransferase system. This is obtained by eliminating the pathways consuming PEP like pyruvates kinases (encoded by the pykA and pykF genes) and/or by promoting the synthesis of PEP e.g. by overexpressing the ppsA gene coding for PEP synthase. Additionally, it is valuable for the enzyme converting pyruvate into acetyl-coA to be resistant to high concentrations of NADH found under anaerobic conditions. This can be obtained by a specific mutation in the lpd gene. Advantageously, the synthesis of the by-product acetate is prevented by attenuating one or several of the genes ackA, pta, poxB.

This invention is also related to a method for the production of 1,2-propanediol at an optimal yield, under aerobic, microaerobic or anaerobic conditions, using said evolved and optionally genetically modified strain of *E. coli* grown in an appropriate growth medium containing a simple carbon source. Additionally, the invention is related to a method for the production of 1,2-propanediol at an optimal yield, under anaerobic conditions, using said evolved and optionally genetically modified strain of *C. acetobutylicum* grown in an appropriate growth medium containing a simple or a complex carbon source. The produced 1,2 propanediol according to this method is subsequently recovered and optionally purified.

BRIEF DESCRIPTION OF THE DRAWINGS

The accompanying drawing that is incorporated in and constitutes a part of this specification exemplifies the invention and together with the description, serves to explain the principles of this invention.

FIG. 1 depicts the genetic engineering of central metabolism in the development of a 1,2-propanediol production system from carbohydrates.

DETAILED DESCRIPTION OF THE INVENTION

As used herein the following terms may be used for interpretation of the claims and specification.

The term 'strain' denotes a genetic variant of a species. Thus the term 'strain of microorganism' denotes a genetic variant of a species of a specific microorganism. The characteristics given for any strain apply also for the corresponding microorganism or vice versa.

According to the invention the terms 'culture', 'growth' and 'fermentation' are used interchangeably to denote the growth of bacteria in an appropriate growth medium containing a simple carbon source.

The term 'carbon source' according to the present invention denotes any source of carbon that can be used by those skilled in the art to support the normal growth of a micro-organism, and which can be hexoses, pentoses, monosaccharides, disaccharaides, oligosaccharides, starch or its derivatives, hemicelluloses, glycerol and combinations thereof.

The term 'appropriate growth medium' according to the invention denotes a medium of known molecular composition adapted to the growth of the micro-organism and designed in such a way that it promotes the wanted evolution.

The evolution process according to the invention is a process for the preparation of evolved micro-organisms presenting improved production characteristics, and comprises the following steps:

a) Modification of a micro-organism to obtain an initial strain with a "locked" metabolism where the evolution can only take the desired direction when the cells of the initial strain are grown on an appropriate medium,
b) Growth of the initial strain obtained above on said appropriate medium in order to cause it to evolve, wherein the initial strain is grown under aerobic, micro-aerobic or anaerobic conditions,
c) Selection of the "evolved strains" able to grow under these specific conditions, presenting improved production characteristics for the desired compound.

This evolution process has been extensively described in the patent applications WO 2004/076659 filed on Feb. 17, 2004, and WO 2005/073364 filed on Dec. 1, 2005, by the same applicants.

The term 'selection' according to the invention denotes a process wherein the only strains of microorganisms that are retained in the culture medium are those presenting a better fitness under the selection pressure conditions. Typically, the fittest strains are outgrowing their competitors and are then selected. A simple way to select a specific evolved strain of microorganism in a population consists in growing the population in continuous culture in which slow-growing strains are eventually eluted from the culture. This is not an exclusive example for selection, and other methods of selection known by the expert in the field may be applied.

The term 'isolation' denotes a process where an individual strain presenting specific genetic modifications is separated from a population of strains presenting different genetic characteristics. This is done by sampling the biomass after the period of evolution and spreading it on Petri dishes to isolate single colonies.

The term "1,2-propanediol production rate" means a production rate expressed in g/l/h, that is calculated as follows:

Concentration of 1,2-propanediol produced in the
medium (g/l)/time necessary for this production
(hour)

Additionally, a specific production rate expressed in g/g/h, taking into account the quantity of biomass can be calculated as follows:

Concentration of 1,2-propanediol produced in the
medium (g/l)/concentration of biomass produced
in the medium (g/l)/time necessary for these productions (h)

The concentration of biomass is determined either by measuring the absorbance of the fermentation broth with a spectrophotometer reading for example at 600 nm or by determining the dry weight of cells after drying a defined volume of fermentation broth.

The quantity of 1,2-propanediol produced is measured by high performance liquid chromatography (HPLC) with an adapted column according to a state of the art protocol.

In the present invention, evolved strains are selected for the following characteristics: an increased glucose uptake rate and an improved 1,2 propanediol production rate. The strains showing these characteristics are then isolated, and advantageously compared to each other, in the way to identify the best producer.

The glucose uptake rate, expressed in g/l/h is calculated as follow:

Concentration of glucose consumed by the culture
(g/l)/time necessary for this consumption (h)

A specific glucose uptake rate can be calculated by taking into account the concentration of biomass in the medium, as previously described.

Glucose uptake rate and 1,2 propanediol production rate are intimately linked. If the consumption of glucose is increased, the production of the products from the glucose metabolism is increased in the same proportion.

After selection and isolation, the best evolved strains present a glucose uptake that is about 20% higher than the uptake of the initial strain, preferentially about 30% higher or more, more preferentially 50% higher.

The increased 1,2 propanediol production rate is of about 20% higher than the production rate of the initial strain, preferentially about 30% higher or more, more preferentially about 50% higher.

The tpiA gene encodes the enzyme 'triose phosphate isomerase', which catalyses the interconversion of DHAP and GA3P (see FIG. 1). The purpose of the attenuation of this gene is to engineer the metabolism of the cell in such a way that the evolution toward the most efficient 1,2-propanediol production becomes possible.

The term 'attenuation of the expression of a gene' according to the invention denotes the partial or complete suppression of the expression of a gene, which is then said to be 'attenuated'. This suppression of expression can be either an inhibition of the expression of the gene, the suppression of an activating mechanism of the gene, a deletion of all or part of the promoter region necessary for the gene expression, or a deletion in the coding region of the gene. Preferentially, the attenuation of a gene is essentially the complete deletion of that gene, which gene can be replaced by a selection marker gene that facilitates the identification, isolation and purification of the strains according to the invention. A gene is preferentially inactivated by the technique of homologous recombination as described in Datsenko, K. A. & Wanner, B. L. (2000) "One-step inactivation of chromosomal genes in *Escherichia coli* K-12 using PCR products". Proc. Natl. Acad. Sci. USA 97: 6640-6645. Other methods are described below.

The term "expression" refers to the transcription and translation of a gene sequence leading to the generation of the corresponding protein, product of the gene.

The term "reconstructing a functional tpiA gene in the evolved strain" means that the selected evolved strain is modified after the process of evolution by introducing a functional tpiA gene; this can be accomplished by replacing via homologous recombination the attenuated copy of the gene by a wild-type functional copy, thus restoring a triose phosphate isomerase activity similar to the activity measured in the initial strain, or by the introduction of a functional tpiA gene on a different chromosomal locus or by introducing a functional tpiA gene on a plasmid. This restoration can allow a yield of 1,2-propanediol production from glucose greater than 1 mole/mole by partly recycling GASP into DHAP for the production of 1,2-propanediol through the action of triose phosphate isomerase.

The purpose of the attenuation of the expression of at least one gene involved in the conversion of methylglyoxal (2-oxo propanal) into lactate is to inhibit the conversion of methylglyoxal into lactate, so that the methylglyoxal present is used by the cell machinery essentially for the synthesis of 1,2-propanediol.

Genes involved in the conversion of methylglyoxal into lactate are in particular:
  a gene coding for a glyoxalase, for example the gloA gene coding for glyoxalase I, catalysing the synthesis of lactoyl glutathione from methylglyoxal;
  the aldA and aldB genes coding for a lactaldehyde dehydrogenase (catalysing the synthesis of (S) lactate from (S) lactaldehyde).

The expression of one or more of these genes is advantageously attenuated (or the gene is completely deleted) in the initial strain. Preferentially the gloA gene is deleted.

An additional modification is advantageously made to the initial strain consisting in suppressing the natural glucose fermentation routes, which consume reducing equivalents as NADH and therefore compete with 1,2-propanediol biosynthesis pathway.

In particular, it is advantageous to attenuate the expression of the gene ldhA coding for lactate dehydrogenase catalysing the synthesis of lactate from pyruvate, and the expression of the gene adhE coding for alcohol-aldehyde dehydrogenase catalysing the synthesis of ethanol from acetyl-CoA.

Similarly, it is possible to force the micro-organism to use the pyruvate dehydrogenase complex to produce acetyl-CoA and NADH from pyruvate. This can be achieved by attenuating the expression of genes pflA and pflB coding for pyruvate formate lyase.

Attenuation of at least one of the genes edd and eda coding for the enzymes involved in the Entner-Doudoroff pathway, is also useful to prevent the direct metabolism of glucose into glyceraldehyde-3-phosphate and pyruvate that can bypass the 1,2-propanediol synthesis pathway.

Under anaerobic or microaerobic conditions, availability of NADH for the reduction of the precursors into 1,2-propanediol is advantageously increased. This is obtained by alleviating the repression on the tricarboxylic acid cycle mediated by the global regulator ArcA (encoded by the arcA gene). NADH concentration in the cell can also be increased by inactivating the NADH dehydrogenase II encoded by the gene ndh. Therefore, preferably, at least one gene selected among arcA and ndh has its expression attenuated.

Preferentially, the initial strain is selected from the group consisting of bacteria, yeasts and fungi.

More preferentially, the initial strain is selected from the group consisting of Enterobacteriaceae, Bacillaceae, Clostridiaceae, Streptomycetaceae and Corynebacteriaceae.

In a preferred embodiment of the invention, the initial strain is either *Escherichia coli* or *Clostridium acetobutylicum*.

The evolved strain susceptible to be obtained, and the evolved strain such as obtained by the process previously described, is also an object of the invention.

In this evolved strain, it is advantageous to modify the expression of specific genes, i.e. increasing or attenuating gene expression. These modifications allow to improve the 1,2-propanediol production performance.

To obtain an overexpression of a gene of interest, the man skilled in the art knows different methods, for example:
  Replacement of the endogenous promoter with a stronger promoter.
  Introduction into the microorganism of an expression vector carrying said gene of interest.
  Introduction of additional copies of the gene of interest into the chromosome.

The man skilled in the art knows several techniques for introducing DNA into a bacterial strain. A preferred technique is electroporation, which is well known to those skilled in the art.

To obtain the attenuation of the expression of a gene, different methods are known by the man skilled in the art, and are described below.

In a specific embodiment of the invention, the evolved strain is modified by an attenuation of the glyceraldehyde 3 phosphate dehydrogenase (GAPDH) activity, in order to reduce the flux in the lower part of glycolysis and to redirect it toward the synthesis of DHAP and finally 1,2-propanediol (see FIG. 1). This decreased activity may in particular be obtained by an attenuation of the expression of the gapA gene.

The term "attenuation of the activity of an enzyme" refers to a decrease of activity of the enzyme of interest, compared to the observed activity in an evolved strain before any modification. The man skilled in the art knows numerous means to obtain this result, and for example:
  Introduction of a mutation into the gene, decreasing the expression level of this gene, or the level of activity of the encoded protein.
  Replacement of the natural promoter of the gene by a low strength promoter, resulting in a lower expression.
  Use of elements destabilizing the corresponding messenger RNA or the protein.
  Deletion of the gene if no expression at all is desired.

Advantageously in the evolved strain, the efficiency of sugar import is increased. A strong attenuation of the expression of the gapA gene resulting in a decrease of the carbon flux in the GAPDH reaction by more than 50%, this will result in the synthesis of less than 1 mole of phosphoenolpyruvate (PEP) per mole of imported glucose. The sugar-phosphotransferase system (PTS) usually assuring the import of simple sugars into the cell is coupled to a phosphorylation reaction giving glucose-6-phosphate. The phosphate needed for this reaction is provided by the conversion of PEP into pyruvate. Thus decreasing the amount of PEP produced by reducing the flux through glyceraldehyde-3-phosphate reduces sugar import.

In a specific embodiment of the invention, the sugar might be imported into the microorganism by a sugar import system independent of phosphoenolpyruvate availability. The galactose-proton symporter encoded by the gene galP that does not involve phosphorylation can be utilized. In this case, the imported glucose has to be phosphorylated by glucose kinase encoded by the glk gene. To promote this pathway, the expression of at least one gene selected among galP and glk is increased. As a result the PTS becomes dispensable and may be eliminated by attenuating the expression of at least one gene selected among ptsH, ptsI or crr.

In another specific embodiment of the invention, the efficiency of the PTS is increased by increasing the availability of the metabolite PEP. Due to the attenuation of the gapA activity and of the lower carbon flux toward pyruvate, the amount of PEP in the modified strain of the invention could be limited, leading to a lower amount of glucose transported into the cell.

Various means exist that may be used to increase the availability of PEP in a strain of microorganism. In particular, a mean is to attenuate the reaction PEP→pyruvate. Preferentially, the expression of at least one gene selected among pykA and pykF, coding for the pyruvate kinase enzyme, is attenuated in said strain to obtain this result. Another way to increase the availability of PEP is to favour the reaction pyruvate→PEP, catalyzed by phosphoenolpyruvate synthase by increasing the activity of the enzyme. This enzyme is encoded by the ppsA gene. Therefore, preferentially in the microorganism the expression of the ppsA gene is increased. Both modifications can be present in the microorganism simultaneously.

Especially under anaerobic or microaerobic conditions, it is advantageous that the pyruvate dehydrogenase complex (PDC), converting pyruvate into acetyl-coA has low sensitivity to inhibition by NADH. The term "low sensitivity" is defined with reference to the sensitivity of an unmodified enzyme, as already demonstrated in WO 2005/073364. In particular, such characteristic can be obtained by introducing a specific mutation in the lpd gene (coding for the sub-unit lipoamide dehydrogenase of the PDC) resulting in the replacement of alanine 55 in the protein sequence of the enzyme by a valine.

In another specific embodiment of the invention, the synthesis of the by-product acetate is prevented. Under fully aerobic conditions, the reduced co-factor NADH is preferentially oxidised into NAD+ via the respiratory chain with oxygen as a terminal electron acceptor. Therefore, the synthesis of a co-product (e.g. acetate) is not mandatory. It is preferable to avoid such acetate synthesis to optimize the production of 1,2-propanediol.

To prevent the production of acetate, advantageously the activity of at least one enzyme involved in the synthesis of acetate is attenuated. Preferentially, the expression of at least one gene selected among ackA, pta and poxB is attenuated, all these genes coding for enzymes involved in different acetate biosynthesis pathways (see FIG. 1).

Another object of the invention is a method for preparing 1,2-propanediol wherein an evolved strain such as described previously is grown in an appropriate growth medium containing a carbon source, and then the 1,2-propanediol produced is recovered. The production of 1,2-propanediol is performed under aerobic, microaerobic or anaerobic conditions.

The culture conditions (fermentation) for the micro-organisms according to the invention can be readily defined by those skilled in the art. In particular, bacteria are fermented at temperatures between 20° C. and 55° C., preferably between 25° C. and 40° C., and preferably at about 35° C. for *C. acetobutylicum* and at about 37° C. for *E. coli*.

This process can be carried out either in a batch process, in a fed-batch process or in a continuous process.

The evolved strain may be used to produce 1,2-propanediol under aerobic, micro-aerobic or anaerobic conditions.

'Under aerobic conditions' means that oxygen is provided to the culture by dissolving the gas into the liquid phase. This could be obtained by (1) sparging oxygen containing gas (e.g. air) into the liquid phase or (2) shaking the vessel containing the culture medium in order to transfer the oxygen contained in the head space into the liquid phase. Advantages of the fermentation under aerobic conditions instead of anaerobic conditions is that the presence of oxygen as an electron acceptor improves the capacity of the strain to produce more energy in form of ATP for cellular processes. Therefore the strain has its general metabolism improved.

Micro-aerobic conditions are defined as culture conditions wherein low percentages of oxygen (e.g. using a mixture of gas containing between 0.1 and 10% of oxygen, completed to 100% with nitrogen), is dissolved into the liquid phase.

Anaerobic conditions are defined as culture conditions wherein no oxygen is provided to the culture medium. Strictly anaerobic conditions are obtained by sparging an inert gas like nitrogen into the culture medium to remove traces of other gas. Nitrate can be used as an electron acceptor to improve ATP production by the strain and improve its metabolism.

The culture of strains, during the evolution process and the fermentation process for 1,2-propanediol production, is conducted in fermentors with a culture medium of known set composition adapted to the bacteria used, containing at least one carbon source. In particular, a mineral growth medium for *E. coli* can thus be of identical or similar composition to M9 medium (Anderson, 1946, *Proc. Natl. Acad. Sci. USA* 32:120-128), M63 medium (Miller, 1992; A Short Course in Bacterial Genetics: A Laboratory Manual and Handbook for *Escherichia coli* and Related Bacteria, Cold Spring Harbor Laboratory Press, Cold Spring Harbor, N.Y.) or a medium such as that defined by Schaefer et al. (1999, *Anal. Biochem.* 270: 88-96), and in particular the minimum culture medium named MPG described below:

| | |
|---|---|
| $K_2HPO_4$ | 1.4 g/l |
| Nitrilo Triacetic Acid | 0.2 g/l |
| trace element solution* | 10 ml/l |
| $(NH_4)_2SO_4$ | 1 g/l |
| NaCl | 0.2 g/l |
| $NaHCO_3$ | 0.2 g/l |
| $MgSO_4$ | 0.2 g/l |
| glucose | 20 to 100 g/l |
| $NaNO_3$ | 0.424 g/l |
| thiamine | 10 mg/l |
| $FeSO_4, 7H_2O$ | 50 mg/l |
| yeast extract | 4 g/l |

The pH of the medium is adjusted to 7.4 with sodium hydroxide.
*trace element solution: Citric acid 4.37 g/L, $MnSO_4$ 3 g/L, $CaCl_2$ 1 g/L, $CoCl_2, 2H_2O$ 0.1 g/L, $ZnSO_4, 7H_2O$ 0.10 g/L, $CuSO_4, 5H_2O$ 10 mg/L, $H_3BO_3$ 10 mg/L, $Na_2MoO_4$ 8.31 mg/L.

In a specific embodiment of the invention, the method is performed with an evolved strain of *E. coli*, in a growth medium containing a simple carbon source that can be: arabinose, fructose, galactose, glucose, lactose, maltose sucrose or xylose. An especially preferred simple carbon source is glucose.

In another specific embodiment of the invention, the method is performed with an evolved strain of *Clostridium acetobutylicum*, in a growth medium containing a simple or a complex carbon source.

The growth medium for *C. acetobutylicum* can thus be of identical or similar composition to Clostridial Growth Medium (CGM, Wiesenborn et al., Appl. Environm. Microbiol., 54: 2717-2722) or a mineral growth medium as given by Monot et al. (Appl. Environm. Microbiol., 44: 1318-1324) or Vasconcelos et al. (J. Bacteriol., 176: 1443-1450).

The carbon source used for the culture of *C. acetobutylicum* is either a simple or a complex carbon. The simple carbon source can be arabinose, fructose, galactose, glucose, lactose, maltose sucrose or xylose. An especially preferred simple carbon source is glucose. The complex carbon source can be starch or hemicellulose. An especially preferred complex carbon source is starch.

Preferentially, the recovered 1,2-propanediol is furthermore purified. The man skilled in the art knows methods for recovering and purifying the produced 1,2-propanediol. These methods are usual processes.

The invention is described above, below and in the Examples with respect to *E. coli*. Thus the genes that can be attenuated, deleted or over-expressed for the initial and evolved strains according to the invention are defined mainly using the denomination of the genes from *E. coli*. However, this designation has a more general meaning according to the invention, and covers the corresponding genes in other micro-organisms. Using the GenBank references of the genes from *E. coli*, those skilled in the art can determine equivalent genes in other organisms than *E. coli*.

The means of identification of the homologous sequences and their percentage homologies are well-known to those skilled in the art, and include in particular the BLAST programmes that can be used on the National Center for Biotechnology Information website with the default parameters indicated on that website. The sequences obtained can be exploited (aligned) using for example the programmes CLUSTALW that can be used on the European Bioinformatics Institute website, with the default parameters indicated on this website.

The PFAM database (protein families database of alignments and hidden Markov models ), that can be used on the Wellcome Trust Sanger Institute website, is a large collection of alignments of protein sequences. Each PFAM makes it possible to visualise multiple alignments, view protein domains, evaluate distributions among organisms, gain access to other databases and visualise known protein structures.

COGs (clusters of orthologous groups of proteins), that can be used on the National Center for Biotechnology Information website, are obtained by comparing protein sequences derived from 66 fully sequenced genomes representing 44 major phylogenetic lines. Each COG is defined from at least three lines, making it possible to identify ancient conserved domains.

REFERENCES IN THE ORDER OF THE CITATION IN THE TEXT

1. Badia J, Ros J, Aguilar J (1985), *J. Bacteriol.* 161: 435-437.
2. Tran Din K and Gottschalk G (1985), *Arch. Microbiol.* 142: 87-92
3. Cameron D C and Cooney C L (1986), *Bio/Technology,* 4: 651-654
4. Sanchez-Rivera F, Cameron D C, Cooney C L (1987), *Biotechnol. Lett.* 9: 449-454
5. Altaras N E and Cameron D C (1999), *Appl. Environ. Microbiol.* 65: 1180-1185
6. Cameron D C, Altaras N E, Hoffman M L, Shaw A J (1998), *Biotechnol. Prog.* 14: 116-125
7. Altaras N E and Cameron D C (2000), *Biotechnol. Prog.* 16: 940-946
8. Huang K, Rudolph F B, Bennett G N (1999), *Appl. Environ. Microbiol.* 65: 3244-3247
9. Berrios-Rivera S J, San K Y, Bennett G N (2003), *J. Ind. Microbiol. Biotechnol.* 30: 34-40
10. Datsenko K A and Wanner B L (2000), *Proc. Natl. Acad. Sci. USA* 97: 6640-6645
11. Anderson E H (1946), *Proc. Natl. Acad. Sci. USA* 32:120-128
12. Miller (1992), A Short Course in Bacterial Genetics: A Laboratory Manual and Handbook for *Escherichia coli* and Related Bacteria, Cold Spring Harbor Laboratory Press, Cold Spring Harbor, N.Y.
13. Schaefer U, Boos W, Takors R, Weuster-Botz D (1999), *Anal. Biochem.* 270: 88-96
14. Wiesenborn D P, Rudolph R B, Papoutsakis E T (1987), *Appl. Environ. Microbiol.,* 54: 2717-2722
15. Monot F, Martin J R, Petitdemange H, Gay R (1982), *Appl. Environ. Microbiol.* 44: 1318-1324
16. Vasconcelos I, Girbal L, Soucaille P (1994), *J. Bacteriol.* 176: 1443-1450

EXAMPLES

The following examples show:
1—Construction of a modified strain of *E. coli* MG1655 lpd*, ΔtpiA, ΔpflAB, ΔadhE, ΔldhA, ΔgloA, ΔaldA, ΔaldB, Δedd, ΔarcA, Δndh
2—Evolution of said initial strain
3—Reconstruction of the tpiA gene in the selected evolved strain
4—Attenuation of the gapA gene; Deletion of the genes pykA and pykF; Overexpression of the ppsA gene
5—Deletion of the genes ackA-pta, poxB
6—Comparison of several obtained strains for 1,2-propanediol production under aerobic conditions
7—Production of 1,2-propanediol in fed-batch culture with the best strain.

Example 1

Construction of a Modified Strain of *E. coli* MG1655 lpd*, ΔtpiA, ΔpflAB, ΔadhE, ΔldhA, ΔgloA, ΔaldA, ΔaldB, Δedd, ΔarcA, Δndh Able to Evolve Toward Improved 1,2-propanediol Production a) Construction of a Modified Strain *E. coli* MG1655 lpd*, ΔtpiA, ΔpflAB, ΔadhE, ldhA::Km, ΔgloA, ΔaldA, ΔaldB, Δedd The chloramphenicol resistance cassette was eliminated in the strain *E. coli* MG1655 lpd*, ΔtpiA, ΔpflAB, ΔadhE, ldhA::km, ΔgloA, ΔaldA, ΔaldB, Δedd::cm (See WO2005073364) according to Protocol 1.

Protocol 1: Elimination of Resistance Cassettes

The chloramphenicol and/or kanamycin resistance cassettes were eliminated according to the following technique. The plasmid pCP20 carrying the FLP recombinase acting at the FRT sites of the chloramphenicol and/or kanamycin resistance cassettes was introduced into the strain by electroporation. After serial culture at 42° C., the loss of the antibiotic resistance cassettes was checked by PCR analysis with the oligonucleotides given in Table 1.

The presence of the modifications previously built in the strain was checked using the oligonucleotides given in Table 1.

The strain obtained was named *E. coli* MG1655 lpd*, ΔtpiA, ΔpflAB, ΔadhE, ldhA::km, ΔgloA, ΔaldA, ΔaldB, Δedd.

TABLE 1

Oligonucleotides used for checking the insertion of a resistance cassette or the loss of a resistance cassette

| Region name | Names of oligos | SEQ ID | Homology with chromosomal region |
|---|---|---|---|
| tpiA gene (deletion) | cdh | N° 1 | See WO2005073364 |
|  | YIIQ | N° 2 |  |
| pflAB gene | pflABF | N° 3 | See WO2005073364 |
|  | pflABR | N° 4 |  |
| adhE gene | ychGf | N° 5 | See WO2005073364 |
|  | adhECr | N° 6 |  |
| ldhA gene (cassette insertion) | hsIJC | N° 7 | See WO2005073364 |
|  | ldhAC2 | N° 8 |  |
| gloA gene | NemACd | N° 9 | See WO2005073364 |
|  | Rnt Cr | N° 10 |  |
| aldA gene | Ydc F C f | N° 11 | See WO2005073364 |
|  | gapCCr | N° 12 |  |
| aldB gene | aldB C f | N° 13 | See WO2005073364 |
|  | YiaYCr | N° 14 |  |
| edd gene | Eda d | N° 15 | See WO2005073364 |
|  | Zwf r | N° 16 |  |
| ldhA gene (deletion) | ldhAF | N° 17 | 1439724 to 1439743 |
|  | ldhAR | N° 18 | 1441029 to 1441007 |
| arcA gene | arcAF | N° 19 | 4638292 to 4638273 |
|  | arcAR | N° 20 | 4636854 to 4636874 |
| ndh gene | ndhF | N° 21 | 1164722 to 1164742 |
|  | ndhR | N° 22 | 1167197 to 1167177 |
| tpiA gene (reconstruction) | YIIQ | N° 2 | 4109599 to 4109580 |
|  | tpiA R | N° 23 | 4108953 to 4108973 |
| gapA promoter (Ptrc16-gapA) | yeaAF | N° 24 | 1860259-1860287 |
|  | gapAR | N° 25 | 1861068-1861040 |
| pykA gene | pykAF | N° 26 | 1935338 to 1935360 |
|  | pykAR | N° 27 | 1937425 to 1937401 |
| pykF gene | pykFF | N° 28 | 1753371 to 1753392 |
|  | pykFR | N° 29 | 1755518 to 1755495 |

TABLE 1-continued

Oligonucleotides used for checking the insertion of a resistance cassette or the loss of a resistance cassette

| Region name | Names of oligos | SEQ ID | Homology with chromosomal region |
|---|---|---|---|
| ackA-pta genes | B2295 | N° 30 | 2410900 to 2410919 |
|  | YfcCR | N° 31 | 2415164 to 2415145 |
| poxB gene | poxBF | N° 32 | 908475 to 908495 |
|  | poxBR | N° 33 | 910375 to 910352 | b) Construction of a Modified Strain *E. coli* MG1655 lpd*, ΔtpiA, ΔpflAB, ΔadhE, ΔldhA::cm, ΔgloA, ΔaldA, ΔaldB, Δedd In order to eliminate the kanamycin resistance cassette and to inactivate the ldhA gene, the chloramphenicol resistance cassette was inserted into the ldhA gene deleting most of the gene concerned according to Protocol 2.

Protocol 2: Introduction of a PCR product for Recombination and Selection of the Recombinants The oligonucleotides chosen and given in Table 2 for replacement of a gene or an intergenic region were used to amplify either the chloramphenicol resistance cassette from the plasmid pKD3 or the kanamycin resistance cassette from the plasmid pKD4 (Datsenko, K. A. & Wanner, B. L. (2000)). The PCR product obtained was then introduced by electroporation into the recipient strain bearing the plasmid pKD46 in which the system λ Red (λ, β, exo) expressed greatly favours homologous recombination. The antibiotic-resistant transformants were then selected and the insertion of the resistance cassette was checked by PCR analysis with the appropriate oligonucleotides given in Table 1.

The other modifications of the strain were checked with the oligonucleotides given in Table 1.

The resulting strain was named *E. coli* MG1655 lpd*, ΔldhA::cm, ΔtpiA, ΔpflAB, ΔadhE, ΔgloA, ΔaldA, ΔaldB, Δedd.

TABLE 2

Oligonucleotides used for replacement of a chromosomal region by recombination with a PCR product in the strain *E. coli* MG1655

| Region name | Names of oligos | SEQ ID | Homology with chromosomal region |
|---|---|---|---|
| ldhA gene | DldhAF | N° 34 | 1440865-1440786 |
|  | DldhAR | N° 35 | 1439878-1439958 |
| arcA gene | DarcAF | N° 36 | 4637868-4637791 |
|  | DarcAR | N° 37 | 4637167-4637245 |
| ndh gene | DndhF | N° 38 | 1165071-1165149 |
|  | DndhR | N° 39 | 1166607-1166528 |
| tpiA gene (reconstruction) | tpiA::kmF | N° 40 | 4109264-4109195 |
|  | tpiA::kmR | N° 41 | 4109109-4109193 |
| gapA promoter (Ptrc16-gapA) | Ptrc-gapAF | N° 42 | 1860478-1860536 |
|  | Ptrc-gapAR | N° 43 | 1860762-1860800 |
| pykA gene | DpykAF | N° 44 | 1935756-1935836 |
|  | DpykAR | N° 45 | 1937055-1937135 |
| pykF gene | DpykFF | N° 46 | 1753689-1753766 |
|  | DpykFR | N° 47 | 1755129-1755051 |
| ackA-pta genes | DackAF | N° 48 | 2411494-2411573 |
|  | DptaR | N° 49 | 2414906-2414830 |
| poxB gene | DpoxBF | N° 50 | 908557-908635 |
|  | DpoxBR | N° 51 | 910262-910180 | c) Construction of a Modified Strain *E. coli* MG1655 ΔarcA::km

The gene arcA was inactivated in strain *E. coli* MG1655 by inserting a kanamycin antibiotic resistance cassette and deleting most of the gene concerned using the technique described in Protocol 2 with the oligonucleotides given in Table 2. The resulting strain was named *E. coli* MG1655 ΔarcA::km.

d) Construction of a Modified Strain of *E. coli* MG1655 lpd*, ΔtpiA, ΔplfAB, ΔadhE, ΔldhA, Δgloa, ΔaldA, ΔaldB, Δedd, ΔarcA The deletion of the gene arcA by replacement of the gene by a kanamycin resistance cassette in the strain *E. coli* MG1655 lpd*, ΔtpiA, ΔpflAB, ΔadhE, ΔldhA::cm, ΔgloA, ΔaldA, ΔaldB, Δedd was performed by the technique of transduction with phage P1.

Protocol 3: Transduction with Phage P1 for Deletion of a Gene

The deletion of the chosen gene by replacement of the gene by a resistance cassette (kanamycin or chloramphenicol) in the recipient *E. coli* strain was performed by the technique of transduction with phage P1. The protocol was in two steps, (i) the preparation of the phage lysate on the strain MG1655 with a single gene deleted and (ii) the transduction of the recipient strain by this phage lysate.

Preparation of the Phage Lysate

Seeding with 100 μl of an overnight culture of the strain MG1655 with a single gene deleted of 10 ml of LB+Cm 30 μg/ml+glucose 0.2%+CaCl$_2$ 5 mM.

Incubation for 30 min at 37° C. with shaking.

Addition of 100 μl of phage lysate P1 prepared on the wild type strain MG1655 (approx. 1×10$^9$ phage/ml).

Shaking at 37° C. for 3 hours until all cells were lysed.

Addition of 200 μl of chloroform, and vortexing.

Centrifugation for 10 min at 4500 g to eliminate cell debris.

Transfer of supernatant in a sterile tube and addition of 200 μl of chloroform.

Storage of the lysate at 4° C.

Transduction

Centrifugation for 10 min at 1500 g of 5 ml of an overnight culture of the *E. coli* recipient strain in LB medium.

Suspension of the cell pellet in 2.5 ml of MgSO$_4$ 10 mM, CaCl$_2$ 5 mM.

Control tubes: 100 μl cells
  100 μl phages P1 of the strain MG1655 with a single gene deleted.

Tube test: 100 μl of cells+100 μphages P1 of strain MG1655 with a single gene deleted.

Incubation for 30 min at 30° C. without shaking.

Addition of 100 μl sodium citrate 1 M in each tube, and vortexing.

Addition of 1 ml of LB.

Incubation for 1 hour at 37° C. with shaking

Plating on dishes LB+Cm 30 μg/ml after centrifugation of tubes for 3 min at 7000 rpm.

Incubation at 37° C. overnight.

The antibiotic-resistant transformants were then selected and the insertion of the deletion was checked by a PCR analysis with the appropriate oligonucleotides given in Table 1.

The resulting strain was named *E. coli* MG1655 lpd*, ΔtpiA, ΔpflAB, ΔadhE, ΔldhA::cm, ΔgloA, ΔaldA, ΔaldB, Δedd, ΔarcA::km.

The chloramphenicol and kanamycin resistance cassettes were then eliminated according to Protocol 1. The strain obtained was named *E. coli* MG1655 lpd*, ΔtpiA, ΔpflAB, ΔadhE, ΔldhA, ΔgloA, ΔaldA, ΔaldB, Δedd, ΔarcA.

e) Construction of a Modified Strain of *E. coli* MG1655 Δndh::km

The gene ndh was inactivated by inserting a kanamycin antibiotic resistance cassette and deleting most of the gene concerned using the technique described in Protocol 2 with the oligonucleotides given in Table 2. The resulting strain was named *E. coli* MG1655 Δndh::km.

f) Construction of a Strain *E. coli* MG1655 lpd*, ΔtpiA, ΔplfAB, ΔadhE, ΔldhA, ΔgloA, ΔaldA, ΔaldB, Δedd, ΔarcA, Δndh The deletion of the gene ndh by replacement of the gene by a kanamycin resistance cassette in the strain *E. coli* MG1655 lpd*, ΔtpiA, ΔplfAB, ΔadhE, ΔldhA, ΔgloA, ΔaldA, ΔaldB, Δedd, ΔarcA was performed as previously using the transduction technique with phage P1 described in Protocol 3.

The resulting strain was named *E. coli* MG1655 lpd*, ΔtpiA, ΔpflAB, ΔadhE, ΔldhA, ΔgloA, ΔaldA, ΔaldB, Δedd, ΔarcA, Δndh::km.

The kanamycin resistance cassette was then eliminated according to Protocol 1. The strain obtained was named *E. coli* MG1655 lpd*, ΔtpiA, ΔpflAB, ΔadhE, ΔldhA, ΔgloA, ΔaldA, ΔaldB, Δedd, ΔarcA, Δndh.

At each step, the presence of the modifications previously built in the strain was checked using the oligonucleotides given in Table 1.

Example 2

Evolution of the Modified Strain *E. coli* MG1655 lpd* ΔtpiA, ΔpflAB, ΔadhE, ΔldhA::cm, ΔgloA, ΔaldA, ΔaldB, Δedd in Chemostat Culture Under Microaerobic Conditions and Physiological Characterization of Evolution To evolve it toward improved 1,2 propanediol production, the strain *E. coli* MG1655 lpd* ΔtpiA, ΔpflAB, ΔadhE, ΔldhA::cm, ΔgloA, ΔaldA, ΔaldB, Δedd was cultivated in continuous culture under anaerobic conditions on one side and under microaerobic conditions (1% oxygen) on the other side in the culture medium MPG such as described previously, with excess glucose (from 20 g/l initially with addition if the glucose becomes exhausted). The temperature was set at 37° C. and the pH was regulated at 6.5 by addition of base. The evolution of the strain in the chemostats was followed by the increase of the biomass concentration coupled with the increase of the concentrations of the product, 1,2-propanediol and the co-product acetate, over several weeks (from 4 weeks up to 6 months). This denoted the improvement of the performances of the strains. When the cultures reached a steady state with no further increase of the concentrations under these conditions, the evolution was done.

The characteristics of the strains before and after evolution were assessed. Single colonies representing individual clones were isolated on Petri dishes. These clones were assessed using the initial strain as control in an Erlenmeyer flask assay, using the same medium MPG used in the chemostat culture. Among these clones, several presented better 1,2-propanediol specific production rates as compared to the control. These clones were selected for the following steps. The results obtained on the best clone for each condition of evolution are reported in Table 4 and 5 below.

TABLE 4

Comparison of the best evolved clone obtained after evolution under anaerobic conditions with the initial strain

| Strain *E. coli* MG1655 lpd* ΔtpiA ΔpflAB ΔadhE ΔldhA::cm ΔgloA Δald, ΔaldB Δedd | Initial strain before evolution (performances measured after 2 days of culture) | Best evolved clone (performances measured after 2 days of culture) |
|---|---|---|
| Glucose specific consumption rate (g glucose/g biomass/h) | 0.12 | 0.21 (+75%) |
| 1,2-propanediol specific production rate (g 1,2-propanediol/g biomass/h) | 0.02 | 0.07 (+250%) |
| 1,2-propanediol + hydroxyacetone specific production rate (g 1,2-propanediol + hydroxyacetone/g biomass/h) | 0.04 | 0.08 (+100%) |

TABLE 5

Comparison of the best evolved clone obtained after evolution under microaerobic conditions with the initial strain

| Strain *E. coli* MG1655 lpd* ΔtpiA ΔpflAB ΔadhE ΔldhA::cm ΔgloA Δald, ΔaldB Δedd | Initial strain before evolution (performances measured after 2 days of culture) | Best evolved clone (performances measured after 2 days of culture) |
|---|---|---|
| Glucose specific consumption rate (g glucose/g biomass/h) | 0.10 | 0.22 (+120%) |
| 1,2-propanediol specific production rate (g 1,2-propanediol/g biomass/h) | 0.01 | 0.08 (+700%) |

TABLE 5-continued

Comparison of the best evolved clone obtained after evolution under microaerobic conditions with the initial strain

| Strain E. coli MG1655 lpd* ΔtpiA ΔpflAB ΔadhE ΔldhA::cm ΔgloA Δald, ΔaldB Δedd | Initial strain before evolution (performances measured after 2 days of culture) | Best evolved clone (performances measured after 2 days of culture) |
|---|---|---|
| 1,2-propanediol + hydroxyacetone specific production rate (g 1,2-propanediol + hydroxyacetone/g biomass/h) | 0.04 | 0.08 (+100%) |

As these clones have been cultivated over an extended period of time on culture medium with yeast extract, they needed to be adapted for the growth in minimal medium. The two best clones whose performances are given in Table 4 and 5 were adapted by serial culture on minimal medium in order to increase their growth rates under such conditions and the adaptation was stopped when their growth rates were stable. Clones from the final culture were isolated and checked to be representative of the adapted population.

Example 3

Reconstruction of tpiA Gene in the Selected Evolved Strain of E. coli MG1655 lpd*, ΔtpiA, ΔpflAB, ΔadhE, ΔldhA::cm, ΔgloA, ΔaldA, ΔaldB, Δedd a) Construction of a Modified Strain E. coli MG1655 tpiA::km A kanamycin antibiotic resistance cassette was inserted upstream of the gene tpiA according to the technique described in Protocol 2 with the oligonucleotides given in Table 2. The resulting strain was named E. coli MG1655 tpiA::km.

Then the reconstruction of the gene tpiA into the evolved strain E. coli MG1655 lpd*, ΔtpiA, ΔpflAB, ΔadhE, ΔldhA::cm, ΔgloA, ΔaldA, ΔaldB, Δedd, ΔarcA, Δndh was performed using the transduction technique with phage P1 described in Protocol 3.

The resulting strain was named evolved E. coli MG1655 lpd*, tpiArc::km, ΔpflAB, ΔadhE, ΔldhA::cm, ΔgloA, ΔaldA, ΔaldB, Δedd, ΔarcA, Δndh.

The kanamycin and chloramphenicol resistance cassettes were then eliminated according to Protocol 2. The strain obtained was named 'evolved E. coli tpiArc'

The presence of the modifications previously built in the strain was checked using the oligonucleotides given in Table 1.

Example 4

Modifications of the 'Evolved E. coli tpiArc':
Attenuation of the gapA Gene; Deletion of the Genes pykA and pykF; Over-Expression of ppsA Gene with a Vector pJB137-PgapA-ppsA a) Replacement of the Natural gapA Promoter with the Synthetic Short Ptrc16 Promoter The replacement of the natural gapA promoter with the synthetic short Ptrc16 promoter (SEQ ID NO 52: gagctgt-tgacgattaatcatccggctcgaataatgtgtggaa) into the strain 'evolved E. coli tpiArc' was made by replacing 225 pb of upstream gapA sequence with FRT-CmR-FRT and an engineered promoter. The technique used is described in Protocol 2 with the oligonucleotides given in Table 2. The resulting strain was named 'evolved E. coli tpiArc' Ptrc16-gapA:: cm.

The chloramphenicol resistance cassette was then eliminated according to Protocol 1. The strain obtained was named 'evolved E. coli tpiArc' Ptrc16-gapA.

b) Deletion of the pykA Gene

The gene pykA is inactivated by inserting a kanamycin antibiotic resistance cassette and deleting most of the gene concerned using the technique described in Protocol 2 with the oligonucleotides given in Table 2. The resulting strain is named 'evolved E. coli tpiArc' Ptrc16-gapA ΔpykA::km.

The kanamycin resistance cassette is then eliminated according to Protocol 1. The strain obtained is named 'evolved E. coli tpiArc' Ptrc16-gapA ΔpykA.

c) Deletion of the pykF Gene

The gene pykF is inactivated by inserting a kanamycin antibiotic resistance cassette and deleting most of the gene concerned using the technique described in Protocol 2 with the oligonucleotides given in Table 2. The resulting strain is named 'evolved E. coli tpiArc' Ptrc16-gapA, ΔpykA, ΔpykF:: km.

As previously, the kanamycin resistance cassette is then eliminated according to Protocol 1. The strain obtained is named 'evolved E. coli tpiArc' Ptrc16-gapA, ΔpykA, ΔpykF.

d) Introduction of an expression vector pJB137-PgapA-ppsA into the Strain

To increase the production of phosphoenolpyruvate the ppsA gene was expressed from the plasmid pJB137 using the gapA promoter. For the construction of plasmid pJB137-PgapA-ppsA, the gene ppsA was PCR amplified from genomic DNA of E. coli MG1655 using the following oligonucleotides:

1. gapA-ppsAF, consisting of 65 bases (SEQ ID NO 53) cctttattcactaacaaatagctggtg-gaatatATGTCCAACAATGGCTCGTCACCGCTGGTGC with:
   a region (upper-case letters) homologous to the sequence (1785106-1785136) of the gene ppsA (1785136 to 1782758), a reference sequence on the website http://genolist.pasteur.fr/Colibri/), and
   a region (lower letters) homologous to the gapA promoteur (1860794-1860761).

2. ppsAR, consisting of 43 bases (SEQ ID NO 54) aatcg-caagcttGAATCCGGTTATTTCTTCAGTTCAGCCAGGC
with:
- a region (upper letters) homologous to the sequence (1782758-1782780) the region of the gene ppsA (1785136 to 1782758)
- a restriction site HindIII (underlined letters)

At the same time the gapA promoter region of the *E. coli* gene gapA was amplified using the following oligonucleotides:
1. gapA-ppsAR, consisting of 65 bases (SEQ ID NO 55) GCACCAGCGGTGACGAGCCATTGTTGGA-CATatattccaccagctatttgttagtgaataaaagg
with:
- a region (upper-case letters) homologous to the sequence (1785106-1785136) of the gene ppsA (1785136 to 1782758), and
- a region (lower letters) homologous to the gapA promoteur (1860794-1860761).
2. gapAF, consisting of 33 bases (SEQ ID NO 56) ACGTC-CCGGGcaagcccaaaggaagagtgaggc
with:
- a region (lower letters) homologous to the gapA promoteur (1860639-1860661).
- a restriction site SmaI (underlined letters)

Both fragments were subsequently fused using the oligonucleotides ppsAR and gapAF (Horton et al. 1989 Gene 77:61-68). The PCR amplified fragment were cut with the restriction enzymes HindIII and SmaI and cloned into the HindIII/SmaI sites of the vector pJB137 (EMBL Accession number: U75326) giving vector pJB137-PgapA-ppsA. Recombinant plasmids were verified by DNA sequencing.

The plasmid pJB137-PgapA-ppsA is introduced into the strain 'evolved *E. coli* tpiArc' Ptrc16-gapA, ΔpykA, ΔpykF.

The strain obtained is named 'evolved *E. coli* tpiArc', Ptrc16-gapA, ΔpykA, ΔpykF, (pJB137-PgapA-ppsA).

At each step, the presence of the modifications previously built in the strain was checked using the oligonucleotides given in Table 1.

Example 5

Construction of a Strain 'Evolved *E. coli* tpiArc' Ptrc16-gapA, ΔpykA, ΔpykF, ΔackA-pta, ΔpoxB (pJB137-PgapA-ppsA) Able to Produce 1,2-Propanediol Without Acetate as By-Product a) Construction of a Modified Strain *E. coli* MG1655 ΔackA-pta::cm The genes ackA and pta are inactivated by inserting a chloramphenicol antibiotic resistance cassette and deleting most of the gene concerned using the technique described in Protocol 2 with the oligonucleotides given in Table 2. The resulting strain is named *E. coli* MG1655 ΔackA-pta::cm.

b) Construction of a Strain 'Evolved *E. coli* tpiArc' Ptrc16-gapA, ΔpykA, ΔpykF, ΔackA-pta The deletion of the genes ackA and pta in the strain 'evolved *E. coli* tpiArc' Ptrc1-gapA, ΔpykA, ΔpykF is performed as previously using the transduction technique with phage P1 as described in Protocol 3.

The resulting strain is named 'evolved *E. coli* tpiArc' Ptrc16-gapA, ΔpykA, ΔpykF, ΔackA-pta::cm.

As previously, the chloramphenicol resistance cassette is then eliminated according to Protocol 1. The strain obtained is named 'evolved *E. coli* tpiArc' Ptrc16-gapA, ΔpykA, ΔpykF, ΔackA-pta.

c) Construction of a Modified Strain 'Evolved *E. coli* tpiArc' Ptrc1-gapA, ΔpykA, ΔpykF, ΔackA-pta, ΔpoxB (pJB137-PgapA-ppsA)

The gene poxB is inactivated by inserting a chloramphenicol antibiotic resistance cassette and deleting most of the gene concerned using the technique described in Protocol 2 with the oligonucleotides given in Table 2.

The resulting strain is named evolved *E. coli* tpiArc Ptrc16-gapA, ΔpykA, ΔpykF, ΔackA-pta, ΔpoxB::cm.

As previously, the chloramphenicol resistance cassette is then eliminated according to protocol 1. The strain obtained is named evolved *E. coli* tpiArc Ptrc16-gapA, ΔpykA, ΔpykF, ΔackA-pta, ΔpoxB.

The plasmid pJB137-PgapA-ppsA is introduced into the strain evolved *E. coli* tpiArc Δtrc1-gapA, ΔpykA, ΔpykF, ΔackA-pta, ΔpoxB. The strain obtained is named evolved *E. coli* tpiArc Ptrc16-gapA, ΔpykA, ΔpykF, ΔackA-pta, ΔpoxB (pJB137-PgapA-ppsA).

At each step, the presence of the modifications previously built in the strain is checked using the oligonucleotides given in Table 1.

Example 6

Comparison of the Different Evolved Strains for 1,2-Propanediol Production Under Aerobic Conditions The strains obtained as described in Example 4 and the control strains (control 1: MG1655 lpd* ΔtpiA ΔpflAB ΔadhE ΔldhA::Cm ΔgloA Δald, ΔaldB Δedd evolved under anaerobic conditions and control 2: MG1655 lpd* ΔtpiA ΔpflAB ΔadhE ΔldhA::Cm ΔgloA Δald, ΔaldB Δedd evolved under microaerobic conditions) were cultivated in an Erlenmeyer flask assay under aerobic conditions in minimal medium supplemented with yeast extract and with glucose as carbon source. The culture was carried out at 34° C. and the pH was maintained by buffering the culture medium with MOPS. At the end of the culture, 1,2-propanediol, acetol and residual glucose in the fermentation broth were analysed by HPLC and the yields of 1,2-propanediol over glucose and 1,2-propanediol+acetol over glucose were calculated. The best strain is then selected for a fermenter fed-batch culture.

| Strain | 1,2-propanediol titer (g/l) | Acetol titer (g/l) | 1,2-propanediol yield (g/g glucose) | 1,2-propanediol + acetol yield (g/g glucose) |
|---|---|---|---|---|
| Control 1 | 1.88 | 2.1 | 0.16 | 0.34 |
| Control 2 | 0.7 | 3.56 | 0.06 | 0.37 |
| 'evolved *E. coli* tpiArc', Ptrc16-gapA, (pJB137- | 0.5 | 2.77 | 0.06 | 0.42 |

| Strain | 1,2-propanediol titer (g/l) | Acetol titer (g/l) | 1,2-propanediol yield (g/g glucose) | 1,2-propanediol + acetol yield (g/g glucose) |
|---|---|---|---|---|
| PgapA-ppsA) (built from control 1) 'evolved E. coli tpiArc', Ptrc16-gapA, (pJB137-PgapA-ppsA) (built from control 2) | 3.71 | 3.85 | 0.20 | 0.41 |

Example 7

Production of 1,2-Propanediol in Fed-Batch Culture with the Best Strain

The best strain selected in the previous experiment is cultivated in a 2 l fermenter using a fed-batch protocol.

The temperature of the culture is maintained constant at 37° C. and the pH is permanently adjusted to values between 6.5 and 8 using an $NH_4OH$ solution. The agitation rate is maintained between 200 and 300 rpm during the batch phase and is increased to up to 1000 rpm at the end of the fed-batch phase. The concentration of dissolved oxygen is maintained at values between 30 and 40% saturation by using a gas controller. When the optical density reaches a value between three and five, the fed-batch is started with an initial flow rate between 0.3 and 0.5 ml/h, and a progressive increase up to flow rate values between 2.5 and 3.5 ml/h. At this point the flow rate is maintained constant for 24 to 48 hours. The medium of the fed is based on minimal media containing glucose at concentrations between 300 and 500 g/l.

The invention claimed is:

1. A method for the preparation of an evolved strain of microorganism for the production of 1,2-propanediol from a carbon source, said method comprising:
  growing an initial strain of *Escherichia coli* under selection pressure in an appropriate growth medium, said initial bacterial strain comprising an attenuation of the expression of the tpiA gene and an attenuation of the expression of at least one gene involved in the conversion of methylglyoxal into lactate, in order to promote evolution in said initial strain,
  then selecting and isolating the evolved strain having an increased 1,2 propanediol production rate,
  then reconstructing a functional tpiA gene in the evolved strain.

2. The method of claim 1, wherein the gene involved in the conversion of methylglyoxal into lactate is selected from the group consisting of: gloA, aldA and aldB and combinations thereof.

3. The method of claim 1, wherein the initial strain of *Escherichia coli* comprises furthermore the attenuation of the expression of at least one of the genes selected among the group consisting of ldhA, pflA, pflB, adhE, edd and eda.

4. The method of claim 1, wherein the initial strain of *Escherichia coli* comprises futhermore the attenuation of at least one gene selected among the group consisting of arcA and ndh.

5. The method of claim 1 wherein the evolved strain is selected and isolated on the basis of its 1,2-propanediol production rate, increased by at least 20% compared to the production rate of the initial strain.

6. A method for preparing 1,2-propanediol comprising:
  preparing an evolved strain of *Escherichia coli* by a method comprising:
    growing an initial strain of *Escherichia coli* under selection pressure in an appropriate growth medium, said initial bacterial strain comprising an attenuation of the expression of the tpiA gene and an attenuation of the expression of at least one gene involved in the conversion of methylglyoxal into lactate, in order to promote evolution in said initial strain,
    then selecting and isolating the evolved strain having an increased 1,2 propanediol production rate,
    then reconstructing a functional tpiA gene in the evolved strain; growing the evolved strain of *Escherichia coli* in a growth medium containing a simple carbon source; and
  recovering the produced 1,2-propanediol.

7. The method according to claim 6, wherein the recovered 1,2-propanediol is furthermore purified.

8. A method for preparing 1,2-propanediol comprising:
  preparing an evolved strain of *Escherichia coli* by a method comprising:
    growing an initial strain of *Escherichia coli* under selection pressure in an appropriate growth medium, said initial bacterial strain comprising an attenuation of the expression of the tpiA gene and an attenuation of the expression of at least one gene involved in the conversion of methylglyoxal into lactate, in order to promote evolution in said initial strain,
    then selecting and isolating the evolved strain having an increased 1,2 propanediol production rate,
    then reconstructing a functional tpiA gene in the evolved strain,
  wherein at least one of the following is met:
    the initial strain comprises an attenuation of tpiA, gloA, aldA, aldB, ldhA, pflA, pflB, adhE, and/or edd,
    a functional tpiA gene was reconstructed;
    the lpd gene has a point mutation leading to a replacement of alanine 55 by valine,
    the expression of the gapA gene is attenuated, and
    the expression of the ppsA gene is increased; growing the evolved strain of *Escherichia coli* in a growth medium containing a simple carbon source; and
  recovering the produced 1,2-propanediol.

9. The method according to claim 8, wherein the recovered 1,2-propanediol is furthermore purified.

* * * * *

```
                         SEQUENCE LISTING

<160> NUMBER OF SEQ ID NOS: 56

<210> SEQ ID NO 1
<211> LENGTH: 20
<212> TYPE: DNA
<213> ORGANISM: Artificial
<220> FEATURE:
<223> OTHER INFORMATION: Oligonucleotide

<400> SEQUENCE: 1
ggtgatgata gttatcgccg                                                 20

<210> SEQ ID NO 2
<211> LENGTH: 20
<212> TYPE: DNA
<213> ORGANISM: artificial
<220> FEATURE:
<223> OTHER INFORMATION: Oligonucleotide

<400> SEQUENCE: 2
cgtgccatcg acagcagtcc                                                 20

<210> SEQ ID NO 3
<211> LENGTH: 30
<212> TYPE: DNA
<213> ORGANISM: artificial
<220> FEATURE:
<223> OTHER INFORMATION: Oligonucleotide

<400> SEQUENCE: 3
agacattaaa aatatacgtg cagctacccg                                      30

<210> SEQ ID NO 4
<211> LENGTH: 30
<212> TYPE: DNA
<213> ORGANISM: artificial
<220> FEATURE:
<223> OTHER INFORMATION: Oligonucleotide

<400> SEQUENCE: 4
```
gtgaaagctg acaacccttt tgatctttta                                   30

<210> SEQ ID NO 5
<211> LENGTH: 22
<212> TYPE: DNA
<213> ORGANISM: artificial
<220> FEATURE:
<223> OTHER INFORMATION: Oligonucleotide

<400> SEQUENCE: 5
ggctcattgc accaccatcc ag                                           22

<210> SEQ ID NO 6
<211> LENGTH: 24
<212> TYPE: DNA
<213> ORGANISM: artificial
<220> FEATURE:
<223> OTHER INFORMATION: Oligonucleotide

<400> SEQUENCE: 6
gaaaagacgc gctgacaata cgcc                                         24

<210> SEQ ID NO 7
<211> LENGTH: 20
<212> TYPE: DNA
<213> ORGANISM: artificial
<220> FEATURE:
<223> OTHER INFORMATION: Oligonucleotide

<400> SEQUENCE: 7
gccatcagca ggcttagccg                                              20

<210> SEQ ID NO 8
<211> LENGTH: 23
<212> TYPE: DNA
<213> ORGANISM: artificial
<220> FEATURE:
<223> OTHER INFORMATION: Oligonucleotide

<400> SEQUENCE: 8
gggtattgtg gcatgtttaa ccg                                          23

<210> SEQ ID NO 9
<211> LENGTH: 31
<212> TYPE: DNA
<213> ORGANISM: artificial
<220> FEATURE:
<223> OTHER INFORMATION: Oligonucleotide

<400> SEQUENCE: 9
gaagtggtcg atgccgggat tgaagaatgg g                                 31

<210> SEQ ID NO 10
<211> LENGTH: 31
<212> TYPE: DNA
<213> ORGANISM: artificial
<220> FEATURE:
<223> OTHER INFORMATION: Oligonucleotide

<400> SEQUENCE: 10
gggttacgtt tcagtgaggc gcgttctgcg g                                 31

<210> SEQ ID NO 11
<211> LENGTH: 31
<212> TYPE: DNA
<213> ORGANISM: artificial

```
<220> FEATURE:
<223> OTHER INFORMATION: Oligonucleotide

<400> SEQUENCE: 11
tgcagcggcg cacgatggcg acgttccgcc g                            31

<210> SEQ ID NO 12
<211> LENGTH: 31
<212> TYPE: DNA
<213> ORGANISM: artificial
<220> FEATURE:
<223> OTHER INFORMATION: Oligonucleotide

<400> SEQUENCE: 12
cacgatgacg accattcatg cctatactgg c                            31

<210> SEQ ID NO 13
<211> LENGTH: 40
<212> TYPE: DNA
<213> ORGANISM: artificial
<220> FEATURE:
<223> OTHER INFORMATION: Oligonucleotide

<400> SEQUENCE: 13
catatttccc tcaaagaata taaaaaagaa caattaacgc                   40

<210> SEQ ID NO 14
<211> LENGTH: 31
<212> TYPE: DNA
<213> ORGANISM: artificial
<220> FEATURE:
<223> OTHER INFORMATION: Oligonucleotide

<400> SEQUENCE: 14
tatgttcatg cgatggcgca ccagctgggc g                            31

<210> SEQ ID NO 15
<211> LENGTH: 24
<212> TYPE: DNA
<213> ORGANISM: artificial
<220> FEATURE:
<223> OTHER INFORMATION: Oligonucleotide

<400> SEQUENCE: 15
ccccggaatc agaggaatag tccc                                    24

<210> SEQ ID NO 16
<211> LENGTH: 29
<212> TYPE: DNA
<213> ORGANISM: artificial
<220> FEATURE:
<223> OTHER INFORMATION: Oligonucleotide

<400> SEQUENCE: 16
gggtagactc cattactgag gcgtgggcg                               29

<210> SEQ ID NO 17
<211> LENGTH: 20
<212> TYPE: DNA
<213> ORGANISM: artificial
<220> FEATURE:
<223> OTHER INFORMATION: Oligonucleotide

<400> SEQUENCE: 17
gccatcagca ggcttagcgc                                         20
```

```
<210> SEQ ID NO 18
<211> LENGTH: 23
<212> TYPE: DNA
<213> ORGANISM: artificial
<220> FEATURE:
<223> OTHER INFORMATION: Oligonucleotide

<400> SEQUENCE: 18
gggtattgtg gcatgtttaa ccg                                           23

<210> SEQ ID NO 19
<211> LENGTH: 20
<212> TYPE: DNA
<213> ORGANISM: artificial
<220> FEATURE:
<223> OTHER INFORMATION: Oligonucleotide

<400> SEQUENCE: 19
cgacaattgg attcaccacg                                               20

<210> SEQ ID NO 20
<211> LENGTH: 21
<212> TYPE: DNA
<213> ORGANISM: artificial
<220> FEATURE:
<223> OTHER INFORMATION: Oligonucleotide

<400> SEQUENCE: 20
gcggtattga aaggttggtg c                                             21

<210> SEQ ID NO 21
<211> LENGTH: 21
<212> TYPE: DNA
<213> ORGANISM: artificial
<220> FEATURE:
<223> OTHER INFORMATION: Oligonucleotide

<400> SEQUENCE: 21
ccgtgagaag aatcgcgatc g                                             21

<210> SEQ ID NO 22
<211> LENGTH: 21
<212> TYPE: DNA
<213> ORGANISM: artificial
<220> FEATURE:
<223> OTHER INFORMATION: Oligonucleotide

<400> SEQUENCE: 22
gcgtagtcgt gtaagtatcg c                                             21

<210> SEQ ID NO 23
<211> LENGTH: 21
<212> TYPE: DNA
<213> ORGANISM: artificial
<220> FEATURE:
<223> OTHER INFORMATION: Oligonucleotide

<400> SEQUENCE: 23
catttccggt ggtgcgattg c                                             21

<210> SEQ ID NO 24
<211> LENGTH: 29
<212> TYPE: DNA
<213> ORGANISM: artificial
<220> FEATURE:
<223> OTHER INFORMATION: Oligonucleotide

<400> SEQUENCE: 24
```
gccacagccg gaatcatact tggtttggg                                29

<210> SEQ ID NO 25
<211> LENGTH: 29
<212> TYPE: DNA
<213> ORGANISM: artificial
<220> FEATURE:
<223> OTHER INFORMATION: Oligonucleotide

<400> SEQUENCE: 25
cgtcaacacc aacttcgtcc catttcagg                                29

<210> SEQ ID NO 26
<211> LENGTH: 23
<212> TYPE: DNA
<213> ORGANISM: artificial
<220> FEATURE:
<223> OTHER INFORMATION: Oligonucleotide

<400> SEQUENCE: 26
ggcaattacc ctcgacgtac cgg                                      23

<210> SEQ ID NO 27
<211> LENGTH: 25
<212> TYPE: DNA
<213> ORGANISM: artificial
<220> FEATURE:
<223> OTHER INFORMATION: Oligonucleotide

<400> SEQUENCE: 27
ccgatggatg atctgttaga ggcgg                                    25

<210> SEQ ID NO 28
<211> LENGTH: 22
<212> TYPE: DNA
<213> ORGANISM: artificial
<220> FEATURE:
<223> OTHER INFORMATION: Oligonucleotide

<400> SEQUENCE: 28
gcgtaacctt ttccctggaa cg                                       22

<210> SEQ ID NO 29
<211> LENGTH: 24
<212> TYPE: DNA
<213> ORGANISM: artificial
<220> FEATURE:
<223> OTHER INFORMATION: Oligonucleotide

<400> SEQUENCE: 29
gcgttgctgg agcaacctgc cagc                                     24

<210> SEQ ID NO 30
<211> LENGTH: 20
<212> TYPE: DNA
<213> ORGANISM: artificial
<220> FEATURE:
<223> OTHER INFORMATION: Oligonucleotide

<400> SEQUENCE: 30
gcatgggtaa acttaaggcg                                          20

<210> SEQ ID NO 31
<211> LENGTH: 20
<212> TYPE: DNA
<213> ORGANISM: artificial

```
<220> FEATURE:
<223> OTHER INFORMATION: Oligonucleotide

<400> SEQUENCE: 31
taatcaccaa cgtatcgggc                                                        20

<210> SEQ ID NO 32
<211> LENGTH: 21
<212> TYPE: DNA
<213> ORGANISM: artificial
<220> FEATURE:
<223> OTHER INFORMATION: Oligonucleotide

<400> SEQUENCE: 32
cgcggcttgg tcgggtaacg g                                                      21

<210> SEQ ID NO 33
<211> LENGTH: 24
<212> TYPE: DNA
<213> ORGANISM: artificial
<220> FEATURE:
<223> OTHER INFORMATION: Oligonucleotide

<400> SEQUENCE: 33
tcgggctatt taaccgttag tgcc                                                   24

<210> SEQ ID NO 34
<211> LENGTH: 100
<212> TYPE: DNA
<213> ORGANISM: artificial
<220> FEATURE:
<223> OTHER INFORMATION: Oligonucleotide

<400> SEQUENCE: 34
gaaactcgcc gtttatagca caaaacagta cgacaagaag tacctgcaac aggtgaacga            60
gtcctttggc tttgagctgg tgtaggctgg agctgcttcg                                 100

<210> SEQ ID NO 35
<211> LENGTH: 101
<212> TYPE: DNA
<213> ORGANISM: artificial
<220> FEATURE:
<223> OTHER INFORMATION: Oligonucleotide

<400> SEQUENCE: 35
ttaaaccagt tcgttcgggc aggtttcgcc tttttccaga ttgcttaagt tttgcagcgt            60
agtctgagaa atactggtca gcatatgaat atcctcctta g                              101

<210> SEQ ID NO 36
<211> LENGTH: 98
<212> TYPE: DNA
<213> ORGANISM: artificial
<220> FEATURE:
<223> OTHER INFORMATION: Oligonucleotide

<400> SEQUENCE: 36
ccccgcacat tcttatcgtt gaagacgagt tggtaacacg caaacgttg aaaagtattt            60 tcgaagcgga aggctatgtg taggctggag ctgcttcg                                   98

<210> SEQ ID NO 37
<211> LENGTH: 99
<212> TYPE: DNA
<213> ORGANISM: artificial
<220> FEATURE:
<223> OTHER INFORMATION: Oligonucleotide
```

<400> SEQUENCE: 37
ccagatcacc gcagaagcga taaccttcac cgtgaatggt ggcgatgatt tccggcgtat    60
ccggcgtaga ttcgaaatgc atatgaatat cctccttag                          99

<210> SEQ ID NO 38
<211> LENGTH: 99
<212> TYPE: DNA
<213> ORGANISM: artificial
<220> FEATURE:
<223> OTHER INFORMATION: Oligonucleotide

<400> SEQUENCE: 38
ctctcacaaa ttcgctcaaa taataaacaa taaactctgt tttttgatct cacccggtaa    60
agtcgcctat cttttcagct gtaggctgga gctgcttcg                          99

<210> SEQ ID NO 39
<211> LENGTH: 100
<212> TYPE: DNA
<213> ORGANISM: artificial
<220> FEATURE:
<223> OTHER INFORMATION: Oligonucleotide

<400> SEQUENCE: 39
gcaacttcaa acgcggacgg ataacgcggt taatactccc caccagcatc attaatccgg    60
ttttaaagta accatgcagc catatgaata tcctccttag                         100

<210> SEQ ID NO 40
<211> LENGTH: 124
<212> TYPE: DNA
<213> ORGANISM: artificial
<220> FEATURE:
<223> OTHER INFORMATION: Oligonucleotide

<400> SEQUENCE: 40
ggggctgacc ttcgctgttg aaccgattaa gctggcgcta tctgaatcgc ttgaaggttt    60
gaataaatga tcacactggc tcaccttcgg gtgggccttt ctgccatatg aatatcctcc   120
ttag                                                               124

<210> SEQ ID NO 41
<211> LENGTH: 106
<212> TYPE: DNA
<213> ORGANISM: artificial
<220> FEATURE:
<223> OTHER INFORMATION: Oligonucleotide

<400> SEQUENCE: 41
gcgaataaag gaagatggcc gccccgcagg gcagcaggtc tgtgaaacag tatagagatt    60
catcggcaca aaggctttgc tttttgtgta ggctggagct gcttcg                  106

<210> SEQ ID NO 42
<211> LENGTH: 100
<212> TYPE: DNA
<213> ORGANISM: artificial
<220> FEATURE:
<223> OTHER INFORMATION: Oligonucleotide

<400> SEQUENCE: 42
agtcatatat tccaccagct atttgttagt gaataaaagc cacacattat tcgagccgga    60
tgattaatag tcaacagctc tgtaggctgg agctgcttcg                         100

```
<210> SEQ ID NO 43
<211> LENGTH: 79
<212> TYPE: DNA
<213> ORGANISM: artificial
<220> FEATURE:
<223> OTHER INFORMATION: Oligonucleotide

<400> SEQUENCE: 43
gctcacatta cgtgactgat tctaacaaaa cattaacacc aactggcaaa attttgtccc      60
atatgaatat cctccttag                                                  79

<210> SEQ ID NO 44
<211> LENGTH: 101
<212> TYPE: DNA
<213> ORGANISM: artificial
<220> FEATURE:
<223> OTHER INFORMATION: Oligonucleotide

<400> SEQUENCE: 44
cgcggcgggt gccaacgttg tacgtatgaa cttttctcac ggctcgcctg aagatcacaa      60
aatgcgcgcg gataaagttc gtgtaggctg gagctgcttc g                        101

<210> SEQ ID NO 45
<211> LENGTH: 101
<212> TYPE: DNA
<213> ORGANISM: artificial
<220> FEATURE:
<223> OTHER INFORMATION: Oligonucleotide

<400> SEQUENCE: 45
cgccgcatcc ggcaacgtac ttactctacc gttaaaatac gcgtggtatt agtagaaccc      60
acggtactca tcacgtcgcc ccatatgaat atcctcctta g                        101

<210> SEQ ID NO 46
<211> LENGTH: 98
<212> TYPE: DNA
<213> ORGANISM: artificial
<220> FEATURE:
<223> OTHER INFORMATION: Oligonucleotide

<400> SEQUENCE: 46
cccatccttc tcaacttaaa gactaagact gtcatgaaaa agaccaaaat tgtttgcacc      60
atcggaccga aaccgaatg taggctggag ctgcttcg                              98

<210> SEQ ID NO 47
<211> LENGTH: 99
<212> TYPE: DNA
<213> ORGANISM: artificial
<220> FEATURE:
<223> OTHER INFORMATION: Oligonucleotide

<400> SEQUENCE: 47
ggacgtgaac agatgcggtg ttagtagtgc cgctcggtac cagtgcacca gaaaccataa     60
ctacaacgtc acctttgtgc atatgaatat cctccttag                           99

<210> SEQ ID NO 48
<211> LENGTH: 100
<212> TYPE: DNA
<213> ORGANISM: artificial
<220> FEATURE:
<223> OTHER INFORMATION: Oligonucleotide

<400> SEQUENCE: 48
cgagtaagtt agtactggtt ctgaactgcg gtagttcttc actgaaattt gccatcatcg     60
```

```
atgcagtaaa tggtgaagag tgtaggctgg agctgcttcg                         100

<210> SEQ ID NO 49
<211> LENGTH: 97
<212> TYPE: DNA
<213> ORGANISM: artificial
<220> FEATURE:
<223> OTHER INFORMATION: Oligonucleotide

<400> SEQUENCE: 49
gctgctgtgc agactgaatc gcagtcagcg cgatggtgta gacgatatcg tcaaccagtg    60
cgccacggga caggtcgcat atgaatatcc tccttag                             97

<210> SEQ ID NO 50
<211> LENGTH: 99
<212> TYPE: DNA
<213> ORGANISM: artificial
<220> FEATURE:
<223> OTHER INFORMATION: Oligonucleotide

<400> SEQUENCE: 50
ccttagccag tttgttttcg ccagttcgat cacttcatca ccgcgtccgc tgatgattgc    60
gcgcagcata tacaggctgc atatgaatat cctccttag                           99

<210> SEQ ID NO 51
<211> LENGTH: 102
<212> TYPE: DNA
<213> ORGANISM: artificial
<220> FEATURE:
<223> OTHER INFORMATION: Oligonucleotide

<400> SEQUENCE: 51
cggttgcagc ttatatcgcc aaaacactcg aatcggcagg ggtgaaacgc atctggggag    60
tcacaggcga ctctctgaac ggtgtaggct ggagctgctt cg                      102

<210> SEQ ID NO 52
<211> LENGTH: 41
<212> TYPE: DNA
<213> ORGANISM: Artificial
<220> FEATURE:
<223> OTHER INFORMATION: synthetic promoter

<400> SEQUENCE: 52
gagctgttga cgattaatca tccggctcga ataatgtgtg g                        41

<210> SEQ ID NO 53
<211> LENGTH: 65
<212> TYPE: DNA
<213> ORGANISM: artificial
<220> FEATURE:
<223> OTHER INFORMATION: Oligonucleotide

<400> SEQUENCE: 53 cctttattc actaacaaat agctggtgga atatatgtcc aacaatggct cgtcaccgct     60
ggtgc                                                                65

<210> SEQ ID NO 54
<211> LENGTH: 43
<212> TYPE: DNA
<213> ORGANISM: artificial
<220> FEATURE:
<223> OTHER INFORMATION: Oligonucleotide

<400> SEQUENCE: 54
```

```
aatcgcaagc ttgaatccgg ttatttcttc agttcagcca ggc                43

<210> SEQ ID NO 55
<211> LENGTH: 65
<212> TYPE: DNA
<213> ORGANISM: artificial
<220> FEATURE:
<223> OTHER INFORMATION: Oligonucleotide

<400> SEQUENCE: 55
gcaccagcgg tgacgagcca ttgttggaca tatattccac cagctatttg ttagtgaata     60
aaagg                                                                 65

<210> SEQ ID NO 56
<211> LENGTH: 33
<212> TYPE: DNA
<213> ORGANISM: artificial
<220> FEATURE:
<223> OTHER INFORMATION: Oligonucleotide

<400> SEQUENCE: 56
acgtcccggg caagcccaaa ggaagagtga ggc                                  33
```